US00PP28476P2

(12) United States Plant Patent

MacGregor et al.

(10) Patent No.: US PP28,476 P2

(45) Date of Patent: Oct. 3, 2017

(54) *GEUM* PLANT NAMED 'MACGEU001'

(50) Latin Name: ***Geum* L.**
Varietal Denomination: MACGEU001

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 0 days.

(21) Appl. No.: 15/330,062

(22) Filed: Aug. 1, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette Para

(74) *Attorney, Agent, or Firm* — Samuel R. McCoy, Jr.

(57) ABSTRACT

'MACGEU001' is a new and distinctive variety of *Geum* hybrid which is characterized by large, semi-double flowers which are scarlet red in color and suffused with peachy-orange tones, tall flowering stems, and a long bloom period. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Geum* L.

Variety denomination: The inventive variety of *Geum* hybrid disclosed herein has been given the variety denomination 'MACGEU001'.

BACKGROUND OF THE INVENTION

The present invention relates to a new and distinct cultivar of *Geum* hybrid, which has been given the variety denomination of 'MACGEU001'. Its market class is PLT/263.1.

Parentage: 'MACGEU001' is the result of a controlled cross-pollination breeding program carried out by the inventors at their commercial nursery in Kirkcudbright, Scotland, in 2012. The inventors performed a controlled cross-pollination of the emasculated seed parent, *Geum* hybrid 'Beech House Apricot' (unpatented), with the pollen parent, *Geum chiloense* 'Red Dragon' (unpatented). Said pollination was performed in an insect proof environment. Seed from said cross was harvested, then germinated, and the resulting seedlings were then grown to a mature size in a protected poly tunnel greenhouse. In 2014, the inventors selected the new *Geum* cultivar for its unique flower and bloom characteristics. This new and distinctive cultivar was given the name 'MACGEU001'.

Asexual Reproduction: Asexual reproduction of 'MACGEU001' was first accomplished in 2014 by way of meristematic tissue culture micro propagation at a laboratory in Rijswijk, the Netherlands. Successive generations have shown that the unique features of the instant cultivar are stable and reproduce true to type.

SUMMARY OF THE INVENTION

The cultivar 'MACGEU001' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Geum* cultivar, 'MACGEU001'.

1. *Geum* 'MACGEU001' exhibits large, semi-double flowers; and
2. *Geum* 'MACGEU001' exhibits unique scarlet red flowers suffused with peachy-orange tones; and
3. *Geum* 'MACGEU001' exhibits long flowering stems; and
4. *Geum* 'MACGEU001' exhibits a long bloom period, from April to September in Kirkcudbright, Scotland.

BOTANICAL DESCRIPTION OF THE PLANT

Figure 1:
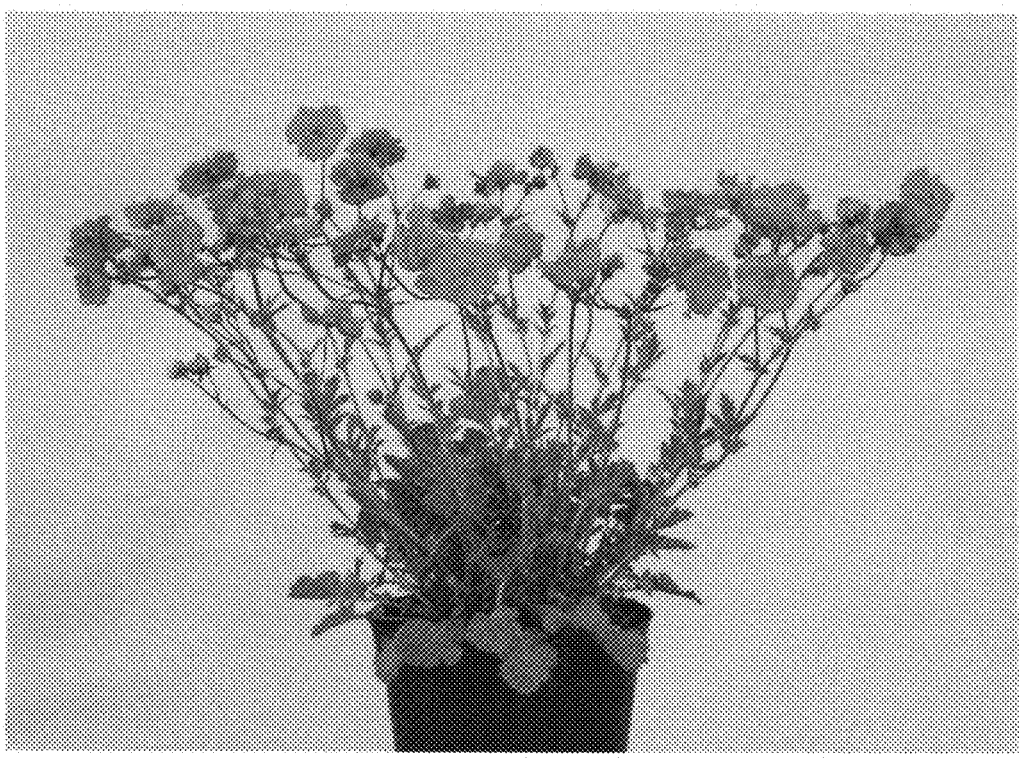
FIG. 1 shows, as nearly true as it is reasonably possible to make the same in color illustrations of this type, the typical foliage and growth characteristics of the new cultivar, 'MACGEU001'. The plant shown is approximately three month old, potted into a 3 liter nursery pot, grown outdoors in Kirkcudbright, Scotland at a commercial nursery.
Figure 2:
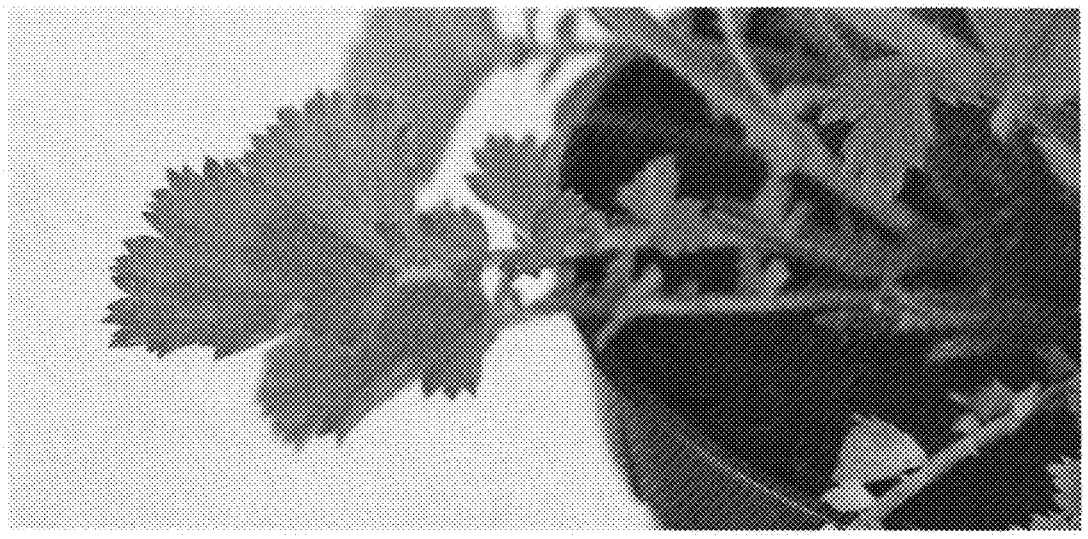
FIG. 2 shows, as nearly true as it is reasonably possible to make the same in color illustrations of this type, the typical foliage of the plant in FIG. 1.
Figure 3:
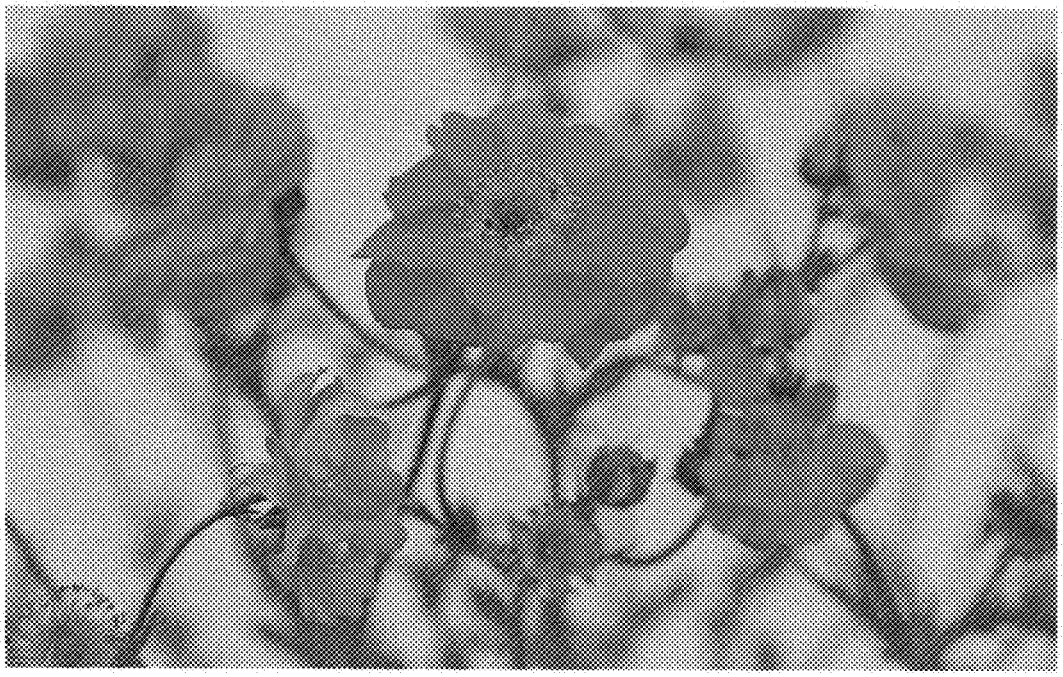
FIG. 3 shows, as nearly true as it is reasonably possible to make the same in color illustrations of this type, the typical flower of the plant in FIG. 1.

The following is a detailed botanical description of a new and distinct variety of *Geum* known as 'MACGEU001', based upon observations of 3 month old greenhouse-grown plants grown in Kirkcudbright, Scotland. Plants were grown using conventional greenhouse production protocols for *Geum* plants including regular overhead irrigation, fertigation feeding, and full sun to partial shade exposure. With the exception of chemical control for thrips insects, no other chemical treatments were given to the plants. Observation data was recorded in May of 2016.

Those skilled in the art will appreciate that certain characteristics will vary with older or, conversely, with younger plants. 'MACGEU001' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'MACGEU001' and comparisons with the parents and most similar variety of common knowledge are provided below.

General plant description:

*Growth habit*.—A broad, obcordate herbaceous perennial with flowering stems arising from the base and no lateral branching present.

*Height*.—17.0 cm to the top of the foliar plane; 34.4 cm to the top of the floral plane.

*Spread*.—60.3 cm.

*Plant vigor*.—Moderate.

*Growth rate*.—Moderate.

*Propagation*.—Meristematic tissue culture.

*Time to produce flowering plant from rooted cutting*.—At 8 to 10 degrees Celsius, approximately 8 to 10 weeks from a tissue culture to a saleable 17 cm pot; no pinching is required.

*Pest resistance and susceptibility*.—Not any more or less susceptible to pests or diseases known to effect *Geum*.

*Environmental tolerances*.—Adapt to, at least, USDA Zones 5 to 9 and temperatures ranging from minus 25 degrees Celsius to 35 degrees Celsius; low to moderate tolerance to rain; moderate to high tolerance to wind.

Root system: Thin, fibrous, and freely branched.

Stem:

*Branching habit*.—Basally branched; moderately free branching.

*Number of primary (main) stems per plant*.—27.

*Number of secondary (lateral) branches per plant*.—None.

*Appearance and shape*.—Rounded.

*Length*.—26.3 cm.

*Diameter*.—0.3 cm.

*Internode length*.—4.6 cm.

*Luster*.—Very slightly glossy.

*Aspect*.—Average angle of 25 degrees from vertical; stems vary from between 10 to 40 degrees from vertical.

*Strength*.—Strong.

*Color, juvenile*.—Yellow-green, near RHS 144A.

*Color, mature*.—Yellow-green, near RHS 144B to 144C.

*Color at internodes*.—Yellow-green, near RHS 144B to 144C.

*Pubescence*.—Densely pubescent; hairs are soft, white RHS 155A, and 1.0 mm long, on average.

Foliage:

*Arrangement*.—Leaves are borne both basally and on stems; on stems, arrangement is alternate.

*Basal leaves*.—Attachment — Petiolate. Division — Simple. Leaf shape — Lyrate. Dimensions — 10.2 cm long, including petiole, and 5.4 cm in width, on average. Leaf attitude — Leaves in an average angle of 45 degrees to the stem. Leaf apex — Acute. Leaf base — Straight to truncate. Leaf margin — Biserrate. Texture, adaxial and abaxial surfaces — Smooth, pubescent. Pubescence, adaxial and abaxial surfaces — Soft, appressed hairs with an average length of 1.0 mm; colored near RHS NN155D. Luster, adaxial and abaxial surfaces — Very slightly glossy. Color — Juvenile foliage color, adaxial surface — Yellow-green, RHS 144A. Juvenile foliage color, abaxial surface — Yellow-green, RHS 147C. Mature leaf color, adaxial surface — Green, RHS 137B. Mature leaf color, abaxial surface — In between green, RHS 137D, and yellow-green, RHS 147B. Venation — Type — Pinnate. Vein color, adaxial surface — Green, RHS 137B. Vein color, abaxial surface — Yellow-green, RHS 145B. Petiole — Length — 4.6 cm. Diameter — Average of 2.0 mm. Strength — Medium. Color, adaxial surface — Yellow-green, RHS 144B, and tinged greyed-orange, RHS 174A, towards the base. Color, abaxial surface — Yellow-green, RHS 144B to 144C, and tinged greyed-orange, RHS 174B to 174C, towards the base. Texture, adaxial and abaxial surfaces — Densely covered with soft hairs; average length of hairs is 1.75 mm; colored white, RHS 155A. Luster, adaxial and abaxial surfaces — Very slightly glossy. Stipules — None present.

*Leaves borne on the stems*.—Quantity — Approximately 6 leaves per stem. Attachment — Petiolate. Division — Simple. Leaf shape — Trilobate; lobes are cleft to deeply cleft. Lobes — Depth of sinuses — Medium. Sinus orientation — Parallel to slightly convergent. Dimensions — 3.6 cm long, including petiole, and 2.8 cm in width, on average. Leaf attitude — Leaves in an average angle of 45 degrees to the stem. Leaf apex — Narrow acute to acuminate. Leaf base — Acute. Leaf margin — Serrate. Texture, adaxial and abaxial surfaces — Smooth, pubescent. Pubescence, adaxial and abaxial surfaces — Soft, appressed hairs with an average length of 1.0 mm; colored near RHS NN155D. Luster, adaxial and abaxial surfaces — Very slightly glossy. Color — Juvenile foliage color, adaxial surface — Yellow-green, RHS 144A. Juvenile foliage color, abaxial surface — Yellow-green, RHS 147C. Mature leaf color, adaxial surface — Green, RHS 137B. Mature leaf color, abaxial surface — In between green, RHS 137D, and yellow-green, RHS 147B. Venation — Type — Pinnate. Vein color, adaxial surface — Green, RHS 137B. Vein color, abaxial surface — Yellow-green, RHS 145B. Petiole — Length — 1.0 cm. Diameter — Average of 2.0 mm. Strength — Medium. Color, adaxial surface — Yellow-green, RHS 144B, and tinged greyed-orange, RHS 174A, towards the base. Color, abaxial surface — Yellow-green, RHS 144B to 144C, and tinged greyed-orange, RHS 174B to 174C, towards the base. Texture, adaxial and abaxial surfaces — Densely covered with soft hairs; average length of hairs is 1.75 mm; colored white, RHS 155A. Luster, adaxial and abaxial surfaces — Very slightly glossy. Stipules — General — Two leafy stipules present at the base of each leaf. Shape — Obovate. Length — Average of 16 mm. Diameter — Average of 10 mm. Apex — Narrow acute. Base — Cuneate. Color, adaxial surface — Green, RHS 143A to 143B. Color, abaxial surface — Green, RHS 143A, to yellow-green, RHS 144A to 144B. Texture, adaxial and abaxial surfaces — Covered with soft, appressed hairs with an average length of 1.0 mm; colored white, RHS NN155D.

Inflorescence:

*Habit*.—Compound cyme.

*Natural flowering season*.—April to September in Kirkcudbright, Scotland.

*Time to flower or response time*.—Approximately 9 months.

*Dimensions*.—13.7 cm high, including peduncle, and 16.9 cm in diameter.

*Quantity of inflorescence per plant*.—3, on average.

*Quantity of flowers per plant*.—80, on average.

*Quantity of flower buds per plant*.—80, on average.

*Quantity of flowers and flower buds per plant*.—160, on average.

*Peduncles*.—Length — Average of 8.2 cm. Diameter — Average of 2.0 mm. Angle — Average angle to stem is 30 degrees. Strength — Moderately strong to strong. Texture — Smooth and densely pubescent; hairs are soft with an average length of 1.0 mm; colored white, RHS 155A. Luster — Slightly glossy. Color — Yellow-green, RHS 145A, with the upper side tinged greyed-orange, RHS 177A.

*Pedicels*.—Length — Average of 20 mm. Diameter — Average of 1 mm. Angle — Average angle to peduncle is approximately 45 degrees. Strength — Moderately strong. Texture — Smooth and densely pubescent; hairs are soft with an average length of 1.0 mm; colored white, RHS 155A. Luster — Slightly glossy. Color — Yellow-green, RHS 145A, with the upper side tinged greyed-orange, RHS 177A.

Flower buds:

*Shape*.—Deltoid.

*Length*.—Average of 8 mm.

*Diameter*.—Average of 8 mm.

*Texture*.—Smooth and densely pubescent; hairs are soft with an average length of 1.0 mm; colored white, RHS 155A.

*Luster*.—Slightly glossy.

*Color*.—Yellow-green, RHS 145A, and tinged grey-brown, RHS 199B to 199C.

Flower:

*Shape, type*.—Rotate; semi-double.

*Flowering habit*.—Freely.

*Aspect*.—Outwardly to slightly upright.

*Flower longevity on plant*.—Approximately ten days.

*Persistent or self-cleaning*.—Self-cleaning.

*Fragrance*.—Non-fragrant.

*Diameter*.—Average of 45 mm.

*Depth*.—Average of 19 mm.

*Calyx*.—Shape — Rotate. Length — 9 mm. Diameter — 16 mm. Sepals — Arrangement — Rotate; one whorl of sepals which alternate between broad sepals and narrow sepals. Quantity — 10 unfused sepals; 5 broad sepals and 5 narrow sepals. Broad sepals — Shape — Deltoid. Dimensions — 9 mm long and 5 mm wide. Apex — Acute. Base — Straight. Sepal reflex — Strongly reflexed. Margin — Entire. Texture and luster, upper surface — Smooth, glabrous, and very slightly glossy. Texture and luster, lower surface — Smooth, covered with soft appressed hairs, and very slightly glossy; hairs are colored white, RHS 155A. Color — When opening, upper surface — Yellow-green, RHS 144C. When opening, lower surface — Yellow-green, RHS 146C. Fully opened, upper surface — Yellow-green, RHS 147C. Fully opened, lower surface — Yellow-green, RHS 148B. Narrow sepals — Shape — Lanceolate. Dimensions — 4 mm long and 1 mm wide. Apex — Narrow acute. Base — Attenuate. Sepal reflex — Slightly reflexed to outwardly. Margin — Entire. Texture and luster, upper surface — Smooth, glabrous, and very slightly glossy. Texture and luster, lower surface — Smooth, covered with soft appressed hairs, and very slightly glossy; hairs are colored white, RHS 155A. Color — When opening, upper surface — Yellow-green, RHS 144C. When opening, lower surface — Yellow-green, RHS 146C. Fully opened, upper surface — Yellow-green, RHS 147C. Fully opened, lower surface — Yellow-green, RHS 148B.

*Petals*.—Quantity — 13, on average; varying from 8 to 16 petals. Arrangement — Rotate; arranged in three whorls of unfused petals. Length — 18 mm, on average. Width — 22 mm, on average. Shape — Reniform. Apex — Broad emarginate. Base — Broad attenuate. Margin — Entire; moderate undulation. Petal color — When opening, upper surface — Orange, RHS 25A. When opening, lower surface — Orange, RHS 24B, and orange-red, RHS 30D. Fully opened, upper surface — Orange-red; RHS N30A, N30B and 33A. Fully opened, lower surface — Orange-red, RHS 34C and N34D. When fading, upper surface — Red, RHS 40A. When fading, lower surface — Red, RHS 39A. Petal venation color — Fully opened, upper surface — Orange-red, RHS 31A. Fully opened, lower surface — Orange-red; RHS 34C and N34D.

Reproductive organs:

*Stamens*.—Quantity — Approximately 150. Anthers — Shape — Oblong. Dimensions — Approximately 0.8 mm long and 0.3 mm wide. Color — Yellow-orange, RHS 14A. Filaments — Length — 4 mm, on average. Color — Green-yellow, RHS 1B to 1C, and fading to yellow, RHS 12B to 12C; distal portion fading to RHS 28C to 28D when maturing. Pollen — Not detected.

*Pistil*.—Quantity — 60, on average. Length — 0.6 mm. Style — Length — 5.5 mm. Color — Red, RHS 42D. Stigma — Shape — Cleft; two-parted. Length — 0.5 mm. Diameter — 0.8 mm. Color — Red, RHS 53A. Ovary Color — Yellow-green, RHS 144A.

Seed and fruit: No fruit or seeds have been detected to date.

COMPARISONS WITH THE PARENT PLANTS AND MOST SIMILAR VARIETY OF COMMON KNOWLEDGE

Plants of the new cultivar 'MACGEU001' differ from its seed parent, *Geum* hybrid 'Beech House Apricot', by the characteristics described in Chart 1.

CHART 1

| Characteristic | 'MACGEU001' | 'Beech House Apricot' |
|---|---|---|
| Plant height. | 30 to 45 cm. | 15 to 20 cm. |
| Petal count; flower form. | Semi-double. | Single. |
| Flower color. | Scarlet red, suffused with peachy-orange tones. | Pale yellow. |
| Bloom period. | Late spring to autumn. | Early spring to late spring. |

Plants of the new cultivar 'MACGEU001' may be distinguished from its pollen parent and most similar known commercial comparator, *Geum chiloense* 'Red Dragon', by the characteristics described in Chart 2.

CHART 2

| Characteristic | 'MACGEU001' | 'Red Dragon' |
|---|---|---|
| Flower diameter. | 6.0 to 6.5 cm. | 5.0 to 5.5 cm. |
| Petal count; flower form. | Semi-double. | Double. |
| Flower color. | Scarlet red, suffused with peachy-orange tones. | Dark red. |
| Bloom period. | Late spring to autumn. | Early to mid-summer. |

That which is claimed is:

1. A new and distinct variety of *Geum* hybrid plant named 'MACGEU001', substantially as described and illustrated herein.

* * * * *